United States Patent [19]

Dixon

[11] Patent Number: 5,286,192
[45] Date of Patent: Feb. 15, 1994

[54] ORAL IRRIGATION APPARATUS

[76] Inventor: David J. Dixon, #7 3rd St., Ridgefield Park, N.J. 07660

[21] Appl. No.: 901,573

[22] Filed: Jun. 19, 1992

[51] Int. Cl.⁵ ............................................. A61G 17/02
[52] U.S. Cl. ........................................ 433/80; 128/66
[58] Field of Search ..................... 128/66; 433/80, 81, 433/82, 84, 85

[56]  References Cited

U.S. PATENT DOCUMENTS 3,561,433  2/1971  Kovach .................................. 128/66
3,578,884  5/1971  Jacobson .............................. 128/66
3,703,170  11/1972  Ryckman, Jr. ........................ 128/66
4,564,005  1/1986  Marchand et al. .................. 128/66

Primary Examiner—John J. Wilson
Attorney, Agent, or Firm—Leon Gilden

[57]  ABSTRACT

A tool member is arranged to provide a compressed air discharge into a fluid filled chamber to direct fluid from the chamber into one of a plurality of irrigation tools. The irrigation tools are arranged for frictional engagement within a socket of the tool member.

4 Claims, 4 Drawing Sheets

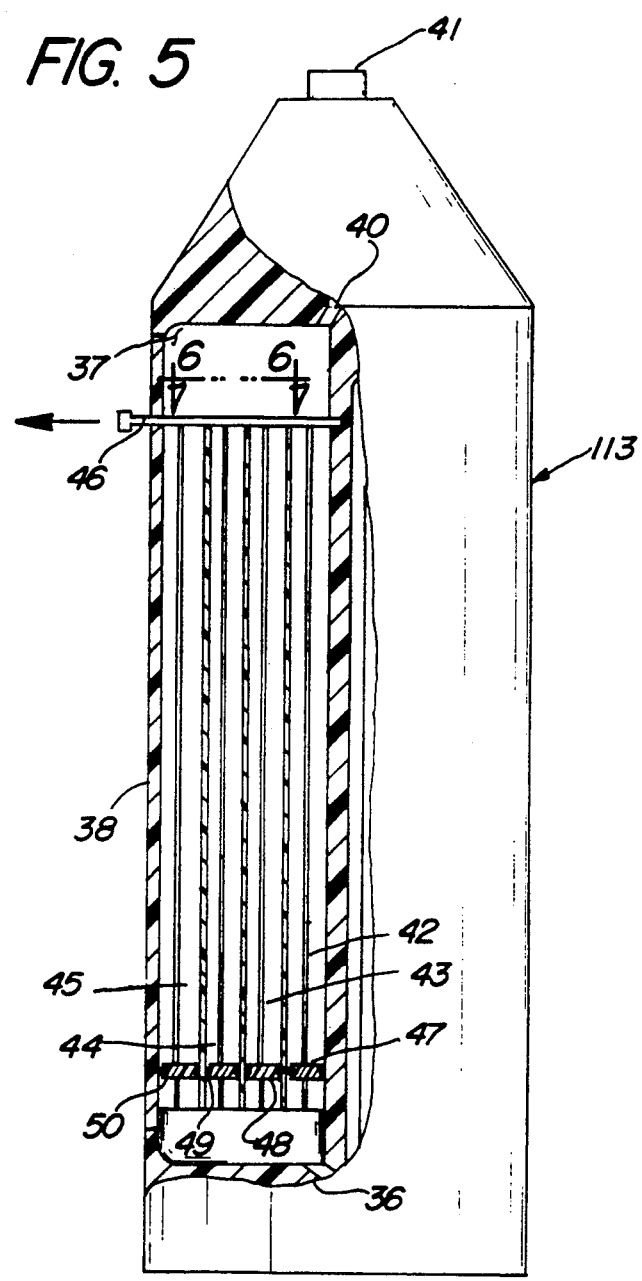
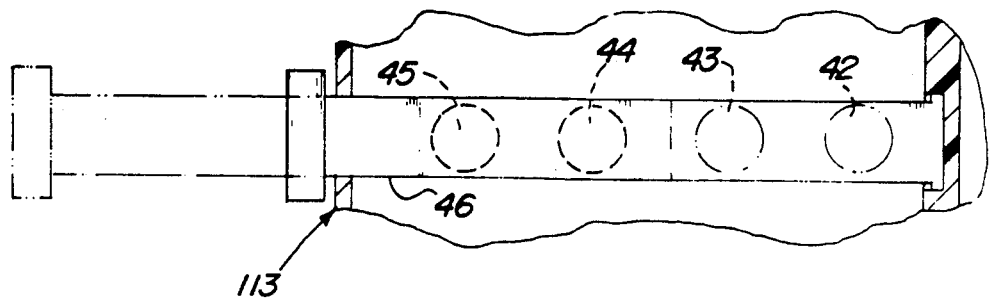

ORAL IRRIGATION APPARATUS

BACKGROUND OF THE INVENTION

1. Field of the Invention

The field of invention relates to oral hygiene tool structure, and more particularly pertains to a new and improved oral irrigation apparatus wherein the same is arranged to direct fluid to an individual's mouth for prevention of oral disease.

2. Description of the Prior Art

The oral regions of the mouth require frequent and periodic care to include brushing and the like. Prior art has developed various devices to direct pressurized fluid into oral regions of the mouth in streams or pulses to provide for irrigation of the mouth and its cleaning. Further, individuals utilizing oral braces and the like utilize fluid directed cleaning to provide for proper massaging cleaning about the brace area.

The instant invention attempts to overcome deficiencies of the prior art by providing for a portable oral irrigation apparatus arranged to direct fluid under pressure to various portions of an individual's mouth. Prior art structure is exemplified by the U.S. Pat. Nos. 4,257,433; 4,803,974; 4,787,845; 4,903,687; and 4,793,331.

The examples of the prior art, while of effectiveness in a limited range, fail to provide for the portable and ease of manipulation of the structure of the instant invention and in this respect, the present invention substantially fulfills this need.

SUMMARY OF THE INVENTION

In view of the foregoing disadvantages inherent in the known types of oral fluid tool structure now present in the prior art, the present invention provides an oral irrigation apparatus wherein the same is arranged to provide for a portable fluid delivery tool permitting delivery of sanitizing and cleaning fluid from a fluid container structure within the tool structure into an oral region of an individual's mouth. As such, the general purpose of the present invention, which will be described subsequently in greater detail, is to provide a new and improved oral irrigation apparatus which has all the advantages of the prior art oral fluid tool structure and none of the disadvantages.

To attain this, the present invention provides a tool member arranged to provide a compressed air discharge into a fluid filled chamber to direct fluid from the chamber into one of a plurality of irrigation tools. The irrigation tools are arranged for frictional engagement within a socket of the tool member.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved oral irrigation apparatus which has all the advantages of the prior art oral fluid tool structure and none of the disadvantages.

It is another object of the present invention to provide a new and improved oral irrigation apparatus which may be easily and efficiently manufactured and marketed.

It is a further object of the present invention to provide a new and improved oral irrigation apparatus which is of a durable and reliable construction.

An even further object of the present invention is to provide a new and improved oral irrigation apparatus which is susceptible of a low cost of manufacture with regard to both materials and labor, and which accordingly is then susceptible of low prices of sale to the consuming public, thereby making such oral irrigation apparatus economically available to the buying public.

Still yet another object of the present invention is to provide a new and improved oral irrigation apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an orthographic view of a modified tool member of the invention.

FIG. 6 is an orthographic view, taken along the lines 6—6 of FIG. 5 in the direction indicated by the arrows.

DESCRIPTION OF THE PREFERRED EMBODIMENT

Figure 1:
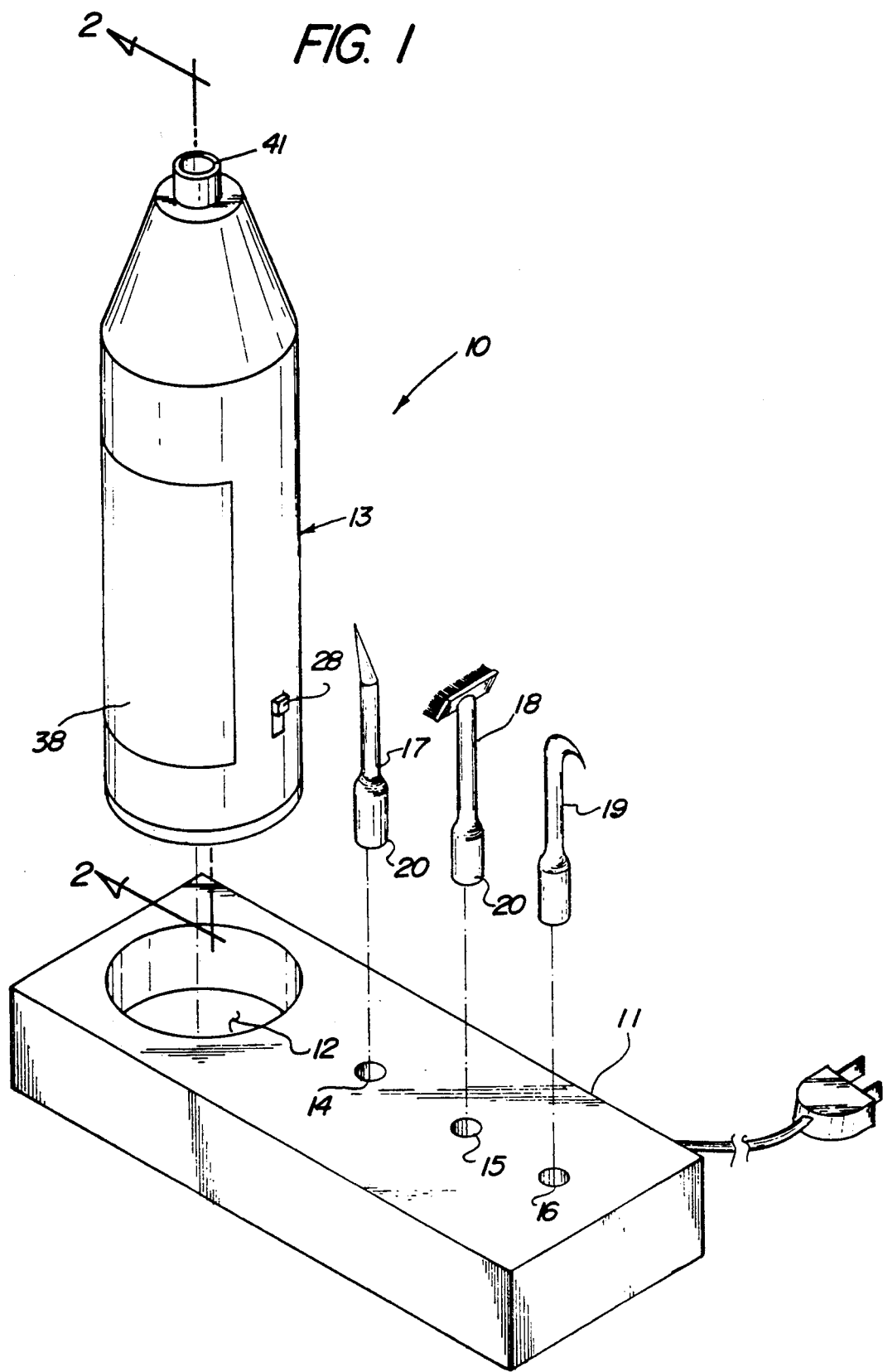
FIG. 1 is an isometric illustration of the instant invention.
Figure 2:
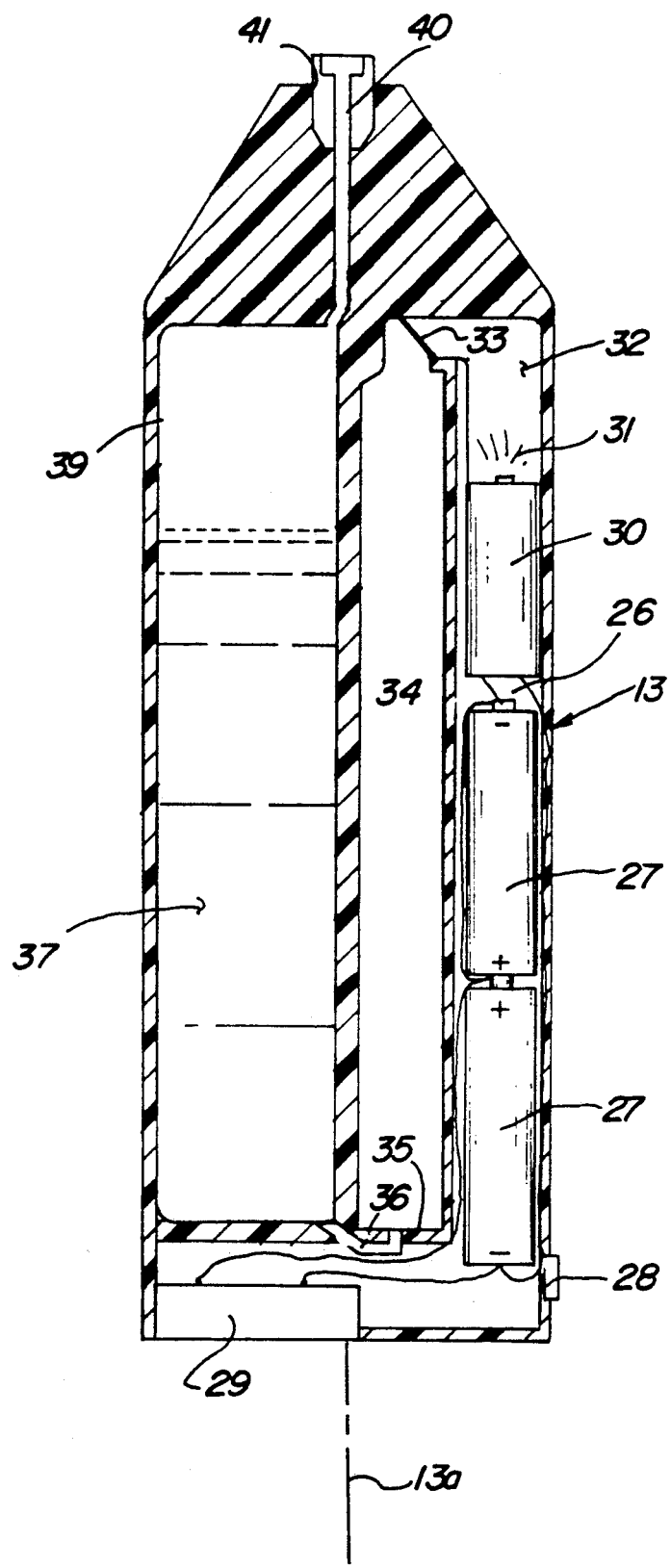
FIG. 2 is an orthographic view, taken along the lines 2—2 of FIG. 1 in the direction indicated by the arrows.
Figure 3:
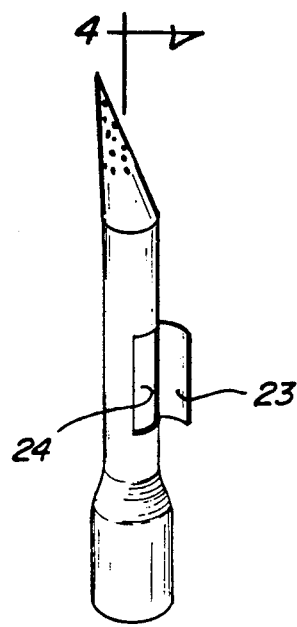
FIG. 3 is an orthographic view of one of the tool heads utilized by the invention.
Figure 4:
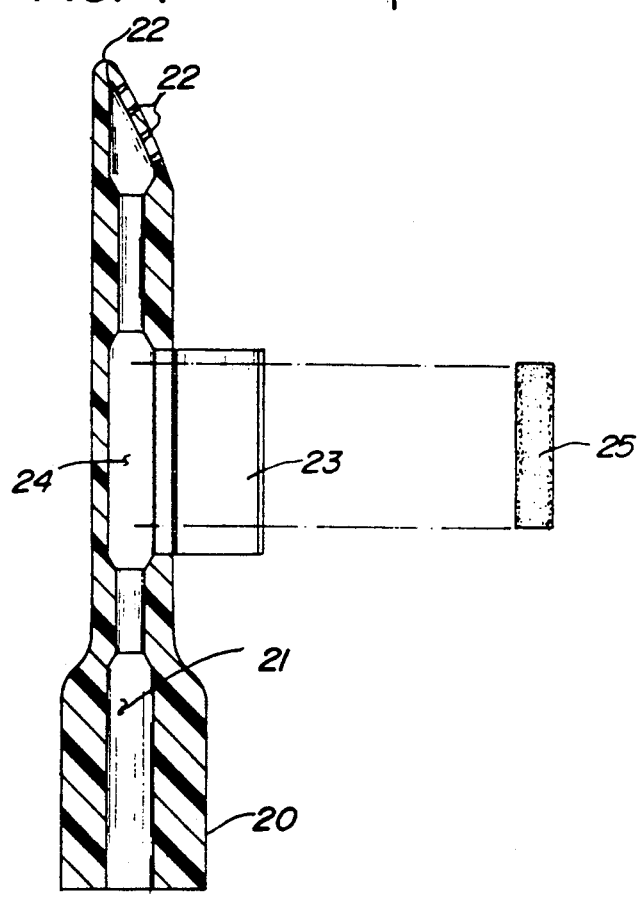
FIG. 4 is an orthographic view, taken along the lines 4—4 of FIG. 3 in the direction indicated by the arrows.

With reference now to the drawings, and in particular to FIGS. 1 to 6 thereof, a new and improved oral irrigation apparatus embodying the principles and concepts of the present invention and generally designated by the reference numeral 10 will be described.

More specifically, the oral irrigation apparatus 10 of the instant invention essentially comprises a support base 11, including a first cavity 12 having electrical recharge capability in operative communication with a base portion of a tool member 13. Such recharge structure per se is of a conventional knowledge and its further view is not deemed necessary. The support base 11 further includes a respective second, third, and fourth cavity 14, 15, and 16 respectively to mount a respective first, second, and third tool head 17, 18, and 19. The first tool head 17 has an upwardly pointed upper end for access to various portions of an oral region of an individual, with the second tool head 18 having a brushing head 18 having a brush member having a matrix of bristles mounted to an upper distal end of the second tool head 18. The third tool head 19 is arranged to provide for a downwardly projecting pointed head for providing further access to various portions of an individual's mouth during an oral cleaning. Each tool head includes a tool head base 20, as exemplified in FIGS. 3 and 4. The tool head base 20 is of a first diameter. Each tool head is further provided with a fluid delivery conduit 21 directed coextensively therethrough having at least one if not a plurality of fluid exit ports 22 at the upper distal end of each tool head. A tool head door 23 is optionally provided through each tool head body for access into a fluid mixing chamber 24 having a chamber diameter greater than a conduit diameter of the fluid delivery conduit 21. A porous flavoring cylinder 25 is arranged for positioning within the fluid mixing chamber 24. Additionally, various antiseptic cylinders and the like may be substituted for the flavoring cylinder.

The tool member 13 is defined about an axis 13a for symmetrical construction and ease of manipulation of the tool member in use. First chamber 26 is arranged in a parallel spaced relationship relative to the axis 13a and includes a plurality of battery members 27, or at least one such battery member, in electrical communication between an on/off switch 28, an electrical AC/DC recharge unit 29, and an air compressor member 30 within the first chamber. The air compressor member 30 includes an outlet port 31 in pneumatic communication with a first pneumatic conduit 32. The first pneumatic conduit 32 includes a check valve plate 33 permitting one-way flow from the first pneumatic conduit 32 into a second pnematic conduit 34 that is arranged parallel to the first pneumatic conduit 32 and a first chamber 36. A second chamber 37 is mounted within the tool member 38 in pneumatic communication with the second pneumatic conduit 34 through a third pneumatic conduit 36 that is directed through the second pneumatic conduit floor 35 into the second chamber 37. An access door 38 directed through an outer wall of the tool member 13 provides access to a fluid bag member 39 for replacement of such bag member in use. The bag member includes an upper bag opening positioned in adjacency relative to a tool fluid conduit 40 that is directed from the second chamber 37 into a tool member resilient socket 41 having an internal diameter equal to the first diameter to resiliently and frictionally engage the tool head base 20 of one of the plurality of tool heads 17-19. In this manner, upon actuation of the compressor member 30, pressurized air is accumulated within the second pneumatic conduit 34 to effect pressurizing of the second chamber 37 and direct fluid therefrom through the tool fluid conduit 40 and subsequently into the fluid delivery conduit 21 of one of the tool heads.

A modified tool member 113, as indicated in FIG. 5, has a second chamber first, second, third, and fourth tube 42, 43, 44, and 45, each arranged for selective filling with various antiseptic and bacterial, as well as flavored, fluids as desired which may be filled on opening of the access door 38. Pressurizing into the second chamber 37 through the floor of the second chamber directs pressurized air to a bottom portion of respective first, second, third, and fourth pistons 47, 48, 49, and 50 slidably mounted within each of the respective first, second, third, and fourth second chamber tubes 42-45. A valve plate 46 at an upper distal end over each of the first, second, third, and fourth tubes is slidingly and radially directed through the access door 38 for displacement of the valve plate 46 providing sequential opening of each of the respective tubes for directing the fluid therefrom through the tool fluid conduit 40 and into an associated tool head 17, 18, or 19. The second chamber first, second, third, and fourth tubes are arranged typically for mounting to the door 38 to permit ease of filling during use.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An oral irrigation apparatus, comprising,
   a support base, the support base including a first cavity, and a tool member having a tool member floor received within the first cavity,
   and
   the support base having at least a second cavity mounting a first tool head therewithin, the first tool head having a tool head base defined by a first diameter, and the tool member defined about a predetermined axis, wherein the tool member includes a tool member resilient socket having an integral diameter equal to the first diameter to receive the tool member base therewithin, wherein the tool member socket is coaxially aligned with the axis at an upper distal end of the tool member, and the first tool head includes a fluid delivery conduit directed coextensively through the first tool member, and at least one fluid exit port directed through the first tool head into fluid communication with the fluid delivery conduit, and a tool head door directed into the first tool head, and a fluid mixing chamber positioned within the first tool head in adjacency relative to the tool head door, the fluid mixing chamber having a chamber diameter and the fluid delivery conduit having a conduit diameter less than the chamber diameter, and at least one cylinder means arranged for reception within the fluid mixing chamber for imparting a predetermined additive into fluid directed through the fluid delivery conduit.

2. An apparatus as set forth in claim 1 wherein the tool member includes a first chamber oriented parallel relative to the axis having at least one battery member therewithin, and an air compressor member mounted within the first chamber at an upper distal end thereof, wherein the air compressor member includes an outlet port in pneumatic communication with a first pneumatic conduit, and an on/off switch in electrical communication between the at least one battery member and the air compressor member to effect selective actuation of the air compressor member, and the on/off switch mounted on the tool member, and a second pneumatic conduit in communication with the first pneumatic conduit, with a check valve oriented at an inner face between the first pneumatic conduit and the second pneumatic conduit, the second pneumatic conduit having a second pneumatic conduit floor, and a second chamber arranged in a spaced relationship relative to the first pneumatic conduit and the second pneumatic conduit within the tool member, and the second chamber having a second chamber floor, and a third pneumatic conduit directed through the second pneumatic conduit floor and through the second chamber floor into the second chamber, and fluid containment means mounted within the second chamber for directing fluid to the tool member socket, and a tool fluid conduit in fluid communication between the second chamber and the tool member socket.

3. An apparatus as set forth in claim 2 wherein the fluid containment means comprises a fluid impermeable bag member mounted within the second chamber, and the bag member having a bag member outlet opening positioned adjacent a lower distal end of the tool fluid conduit, and the tool member having a second chamber access door directed through an outer wall of the tool member into communication with the second chamber to permit selective replacement of the fluid bag member.

4. An apparatus as set forth in claim 2 wherein said fluid containment means includes a respective first, second, third, and fourth tube, with each tube arranged in adjacency relative to one another in a parallel coextensive relationship within the second chamber parallel to the axis, and the first tube including a first piston contained therewithin, the second tube including a second piston contained therewithin, the third tube including a third piston contained therewithin, and the fourth tube including a fourth tube contained therewithin, wherein each piston is arranged for sliding engagement within each respective tube, and the tool member having a tool member door positioned in adjacency to the second chamber, and the access door including the first tube, second tube, third tube, and fourth tube mounted to the door to permit selective filling of each respective tube, and a valve plate slidably directed through the door positioned over the first tube, second tube, third tube, and fourth tube permitting selective fluid flow from the respective first tube, second tube, third tube, and fourth tube into the tool fluid conduit.

* * * * *